United States Patent [19]

Cooper et al.

[11] 4,049,031

[45] Sept. 20, 1977

[54] AUTOMATIC FRACTION COLLECTOR

[75] Inventors: David J. Cooper, Downingtown; George W. Gebhardt, Philadelphia; Joseph R. Valenta, Wayne, all of Pa.; Francis E. Wdzieczkowski, Barrington, N.J.

[73] Assignee: SmithKline Corporation, Philadelphia, Pa.

[21] Appl. No.: 642,704

[22] Filed: Dec. 22, 1975

[51] Int. Cl.² .......................... B67C 3/26; B67C 3/34
[52] U.S. Cl. .................................. 141/284; 23/259; 141/369
[58] Field of Search ............. 23/259; 141/1, 129-131, 141/132, 134, 231, 248, 250, 256, 284, 324, 369, 387, 388, 279, 376, 392

[56] References Cited

U.S. PATENT DOCUMENTS

| 594,630 | 11/1897 | Lindsay | 141/244 |
| 3,168,124 | 2/1965 | Lenkey | 141/284 |
| 3,625,265 | 12/1971 | Gilson | 141/284 |
| 3,838,719 | 10/1974 | Lederer | 141/284 |

*Primary Examiner*—Richard E. Aegerter
*Assistant Examiner*—Frederick R. Schmidt

*Attorney, Agent, or Firm*—Smith, Harding, Earley & Follmer

[57] ABSTRACT

A liquid fraction collector has a first series of containers and a second series of containers, each of the first and second series of containers being arranged in a plurality of groups with means to support each group at a different elevation. A conduit leads upwardly from each container in said first series with the upper ends of the conduits lying in a first row and a conduit leads upwardly from each container in said second series with the upper end of the conduits lying in a second row parallel to the first row. A carriage is mounted above said conduits. The carriage has means to discharge a liquid having an inverted V guide member with one trough over one row and the other trough over the other row and a discharge tube having its discharge end movable from a position over one trough of the guide member to a position over the other trough of the guide member. The carriage is advanced stepwise from one conduit to the next above the said rows from one end of rows to the other end and returned to said one end by moving means. The discharge tube discharges into the conduits of one row as the carriage advances and is moved to cause discharge into the conduits of the other row when the carriage returns by adjusting means.

5 Claims, 9 Drawing Figures

AUTOMATIC FRACTION COLLECTOR

BACKGROUND OF THE INVENTION

In the Chemical Industry in general and in the Pharmaceutical Industry in particular it is frequently desired to collect a large number of fractions of liquid from a chromatographic column. It is known to do this automatically. Heretofore, automatic fraction collectors for liter sized collection vessels have employed a discharge nozzle which is moved in a circular path requiring a generally circular disposition of the collection funnels which supply the collection vessels through tubes. This arrangement places severe practical restrictions on the number of containers employed to receive the liquid fractions and the devices lack desired mobility.

Automatic fraction collectors using test tube size collection containers are known to the art and are generally of two types. One type uses a fixed delivery tube and a shifting platform to move test tubes in racks into position under the delivery tube. The other type employs a rotary turntable with multiple collection containers and a delivery tube automatically positioned over successive rings.

In accordance with this invention an improved liquid fraction collector is provided which can provide for the use of a greatly enlarged number of liter sized collection containers in the normal space situation. It avoids the complexity and waste of space inherent in the circular and moving platform type devices and is very mobile.

BRIEF SUMMARY OF THE INVENTION

A liquid fraction collector has a first series of containers and a second series of containers, a conduit leads upwardly from each container in said first series with the upper ends of the conduits lying in a first row and a conduit leads upwardly from each container in said second series with the upper end of the conduits lying in a second row parallel to the first row. A carriage is mounted above said conduits. The carriage has means to discharge a liquid. The carriage is advanced stepwise from one conduit to the next from one end of the rows to the other end and returned to said one end. The discharge means is adjustable to discharge into the conduits of one row as the carriage advances and to discharge into the conduits of the other row when the carriage returns.

DETAILED DESCRIPTION OF THE INVENTION

Figure 4:
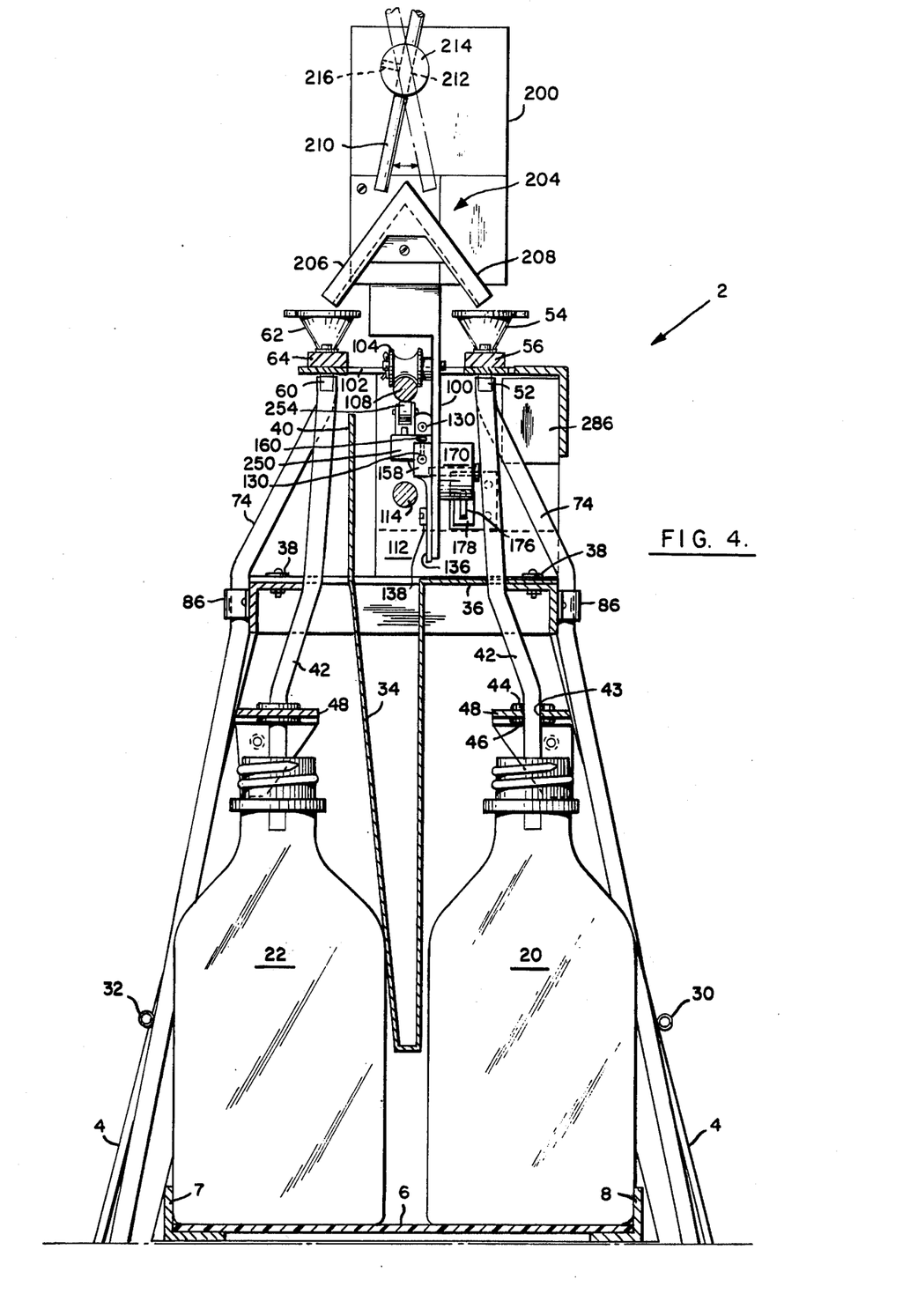
FIG. 4 is a vertical section, partially broken away, taken on the plane indicated by the line 4—4 in FIG. 1.
Figure 5:
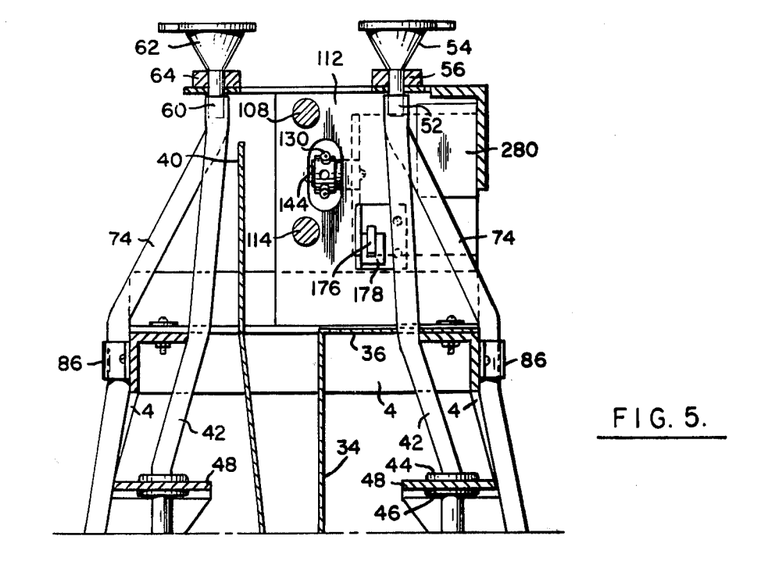
FIG. 5 is a vertical section, partially broken away, taken on the plane indicated by the line 5—5 in FIG. 2.
Figure 8:
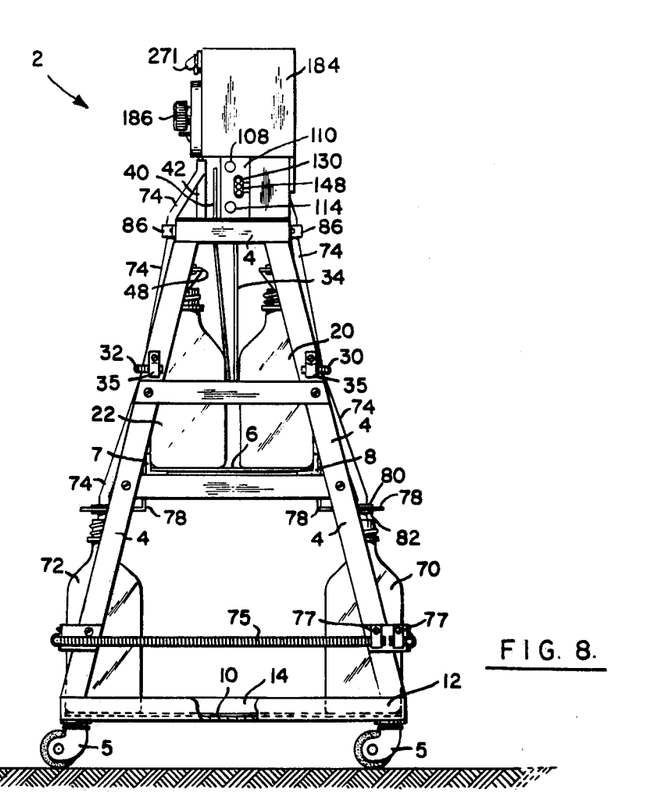
FIG. 8 is a right end elevation of the fraction collector of FIG. 1.

A liquid fraction collector 2 has a frame 4 mounted on casters 5 for ease of movement (FIG. 8). As seen in FIG. 4, an elongated platform 6 is mounted on angle members 7 and 8 which are secured to frame 4. Similarly, an elongated platform 10 is mounted on angle members 12 and 14 which are also secured to frame 4 (FIG. 8). A row of containers 20 is supported by platform 6 and is parallel to a row of containers 22 also supported on platform 6. The containers 20 and 22 are each respectfully restrained by elastic cords 30 and 32 each of which is secured by clips 35, 35. The bottles 20 and 22 are separated by a substantially U-shaped plate 34 (FIG. 4) which has a flange 36 secured to frame 4 by a plurality of bolts indicated at 38 and has an upstanding portion 40 which acts as a protective shield for moving parts to be described hereinafter.

Each bottle 20 and 22 has a clear flexible tube 42 (FIG. 4) discharging into it. Each tube 42 passes through an opening 43 (FIG. 4) in a plate 48. A pair of rubber grommets 44 and 46 on the opposite sides of opening 43 engage the flexible tube 42 tightly to hold it in position. Each tube 42 extending upwardly from a container 20 has its upper end telescoped over the lower end of a stem 52 of a funnel 54 secured to plate 56 which is in turn secured to plates 110 and 112. Each tube 42 extending upwardly from a container 22 has its upper end telescoped over the stem 60 of a funnel 62 which is secured to plate 64 which is in turn secured to plates 110 and 112.

Figure 1:
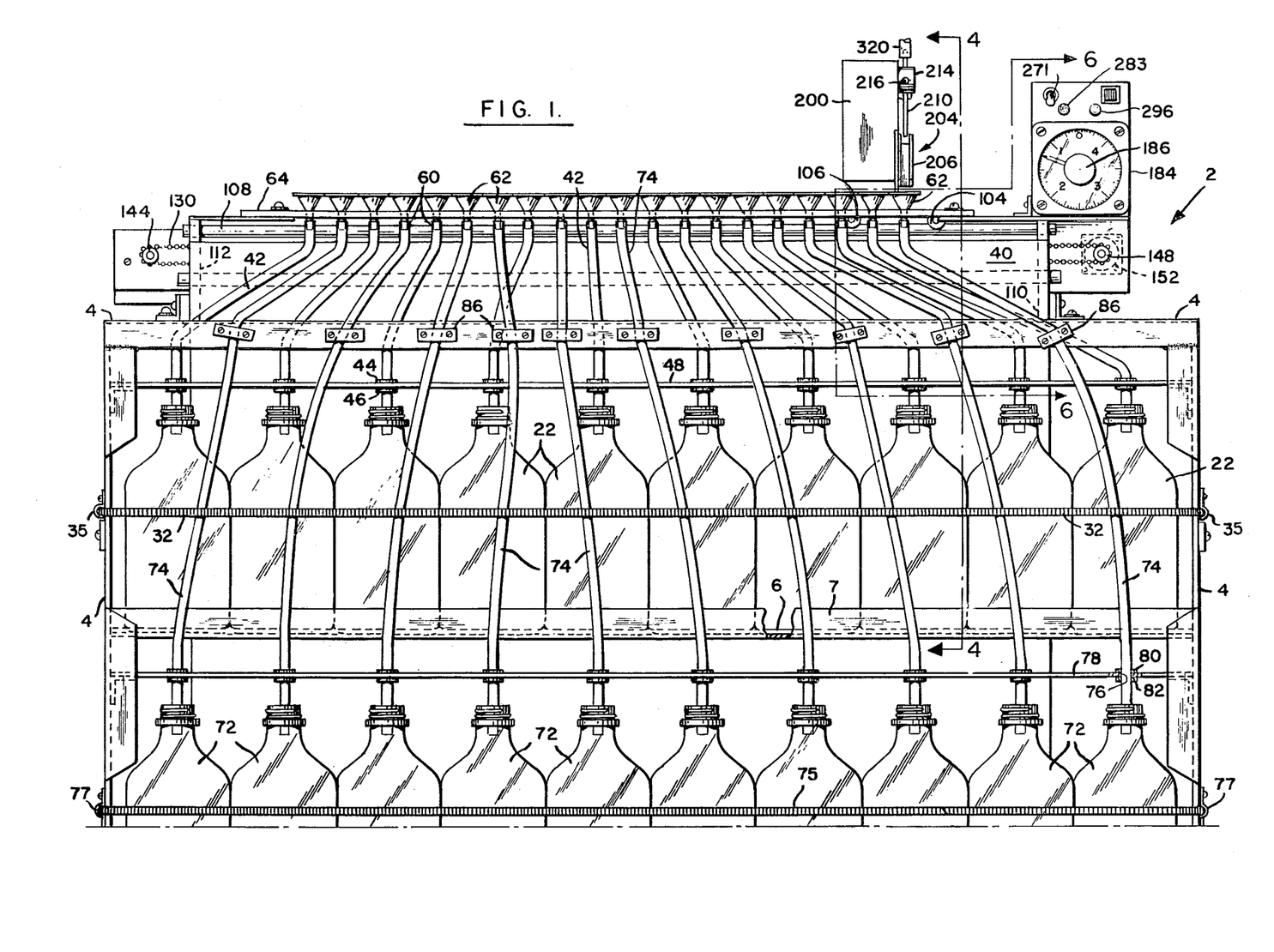
FIG. 1 is a front elevation, partially broken away, of a liquid fraction collector in accordance with the invention.
Figure 2:
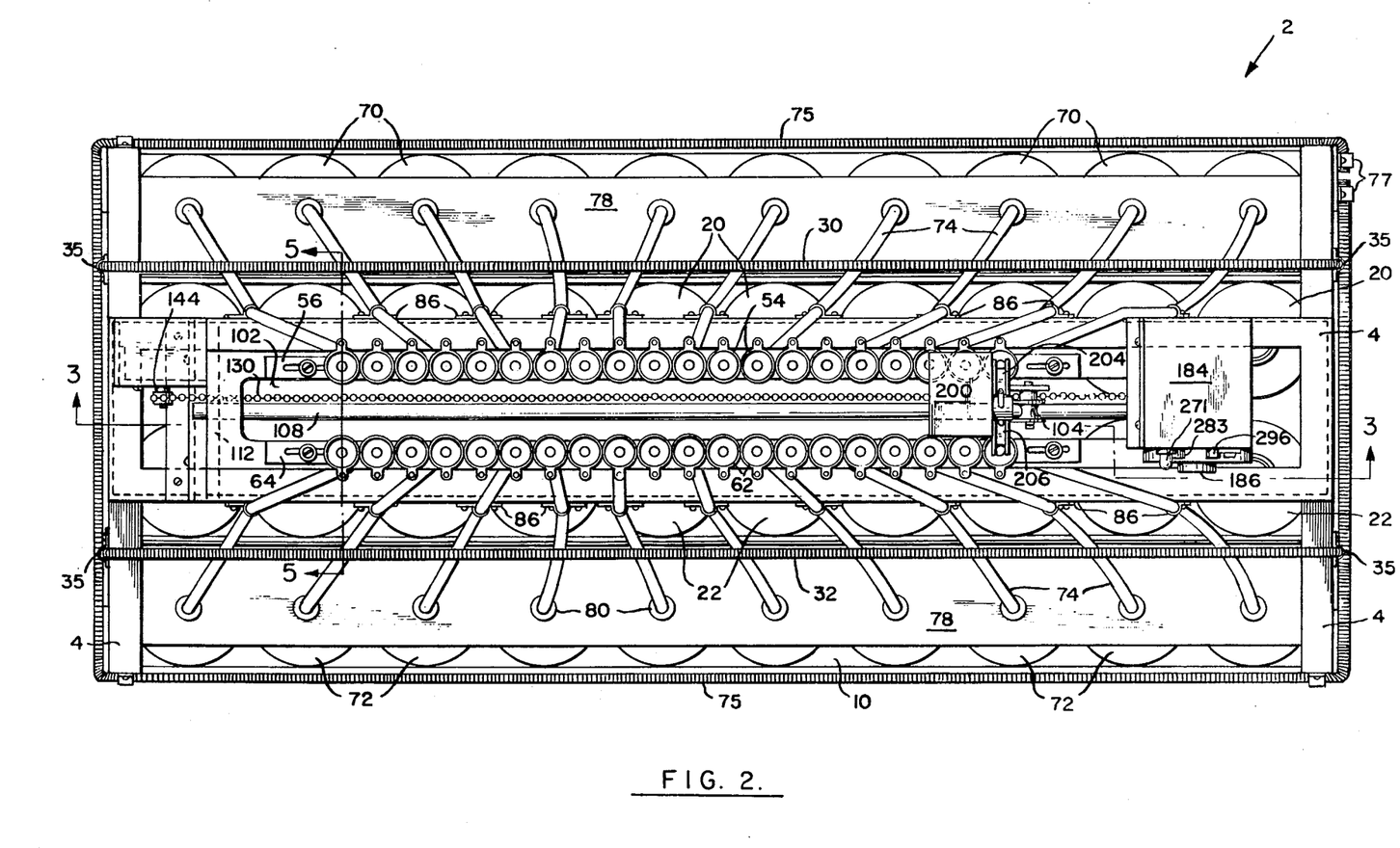
FIG. 2 is a top plan view of the device of FIG. 1.

A row of bottles 70 and a parallel row of bottles 72 are supported on platform 10 (see FIGS. 8 and 2). Bottles 70 and 72 are restrained by an elastic cord 75 secured to frame 4 by clips 77. A clear flexible tube 74 discharges into each bottle 70 and 72 and passes through an opening 76 (FIG. 1) in a plate 78 secured to frame 4 (FIG. 8). A pair of rubber grommets 80 and 82 on opposite sides of each opening 76 (FIG. 1) tightly hold each tube 74 to secure it in position. Each tube 74 is also held in position by a clip 86 secured to the upper portion of frame 4 (FIG. 1). Each tube 74 extending upwardly from a container 70 has its upper end telescoped over the stem 52 of a funnel 54 and each tube 74 extending upwardly from a container 72 has its upper end telescoped over the stem 60 of a funnel 62.

All of the funnels 54 are in a single row which is parallel to the row in which all the funnels 62 are found.

Figures 3, 7:
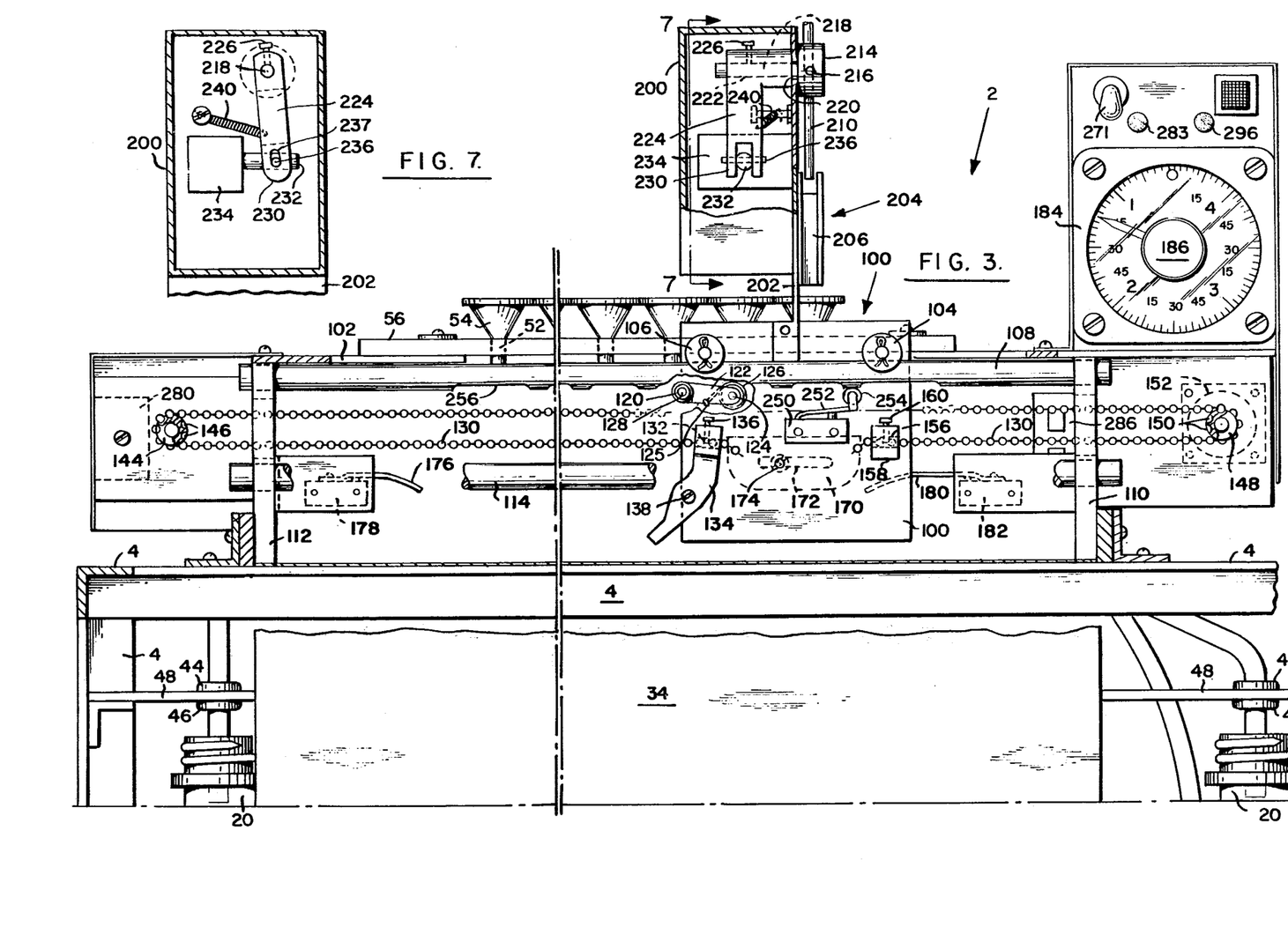
FIG. 3 is a vertical section taken on the plane indicated by the line 3—3 in FIG. 2.
FIG. 7 is a vertical section, partially broken away, taken on the plane indicated by the line 7—7 in FIG. 3.
Figure 6:
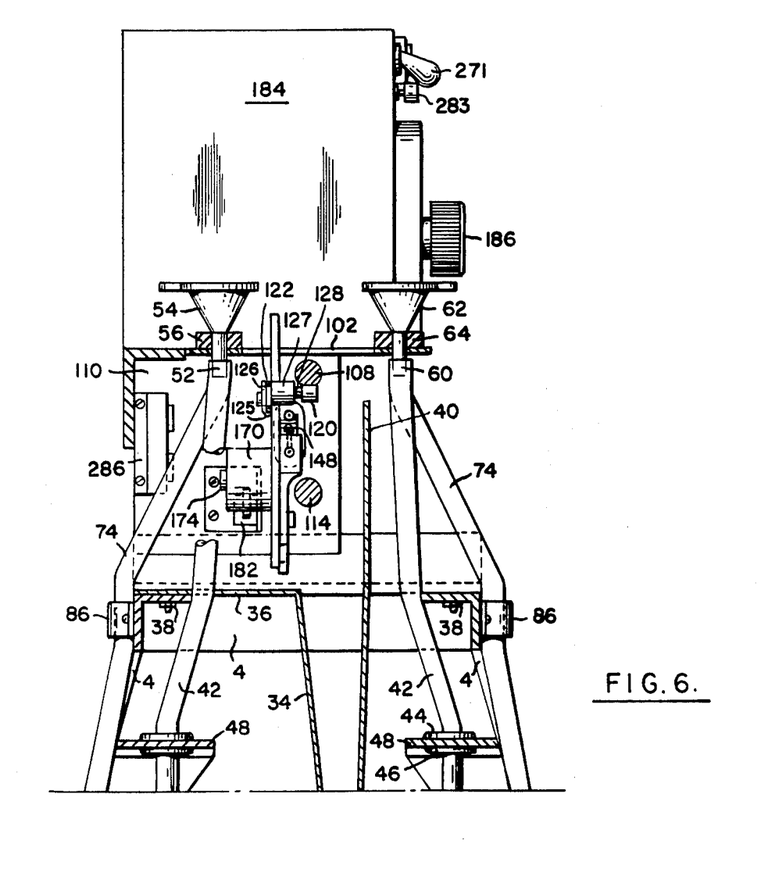
FIG. 6 is a vertical section, partially broken away, taken on the plane indicated by the line 6—6 in FIG. 1.

As seen, for example, in FIG. 3 a carriage 100 extends through an opening 102 and is provided with guide rollers 104 and 106 which ride on a rod 108 secured to plates 110 and 112 which, in turn, are secured to frame 4. Plates 110 and 112 are stiffened by a second row 114 to which they are secured. Plates 56 and 64 are secured to plates 110 and 112. A roller 120 is mounted on lever 122 which is pivotally mounted on rod 124 fixedly secured to carriage 100 and spring biased upwardly by a coil spring 126 having its inner end (not shown) secured to rod 124 and its outer end 125 engaging lever 122. Lever 122 carries a block 127 (FIG. 6) to which is secured a rod 128 on which roller 120 is mounted. Roller 120 engages the underside of rod 108.

A ball chain 130 (FIG. 3) has one end passing through a bore 132 in lever 134 in which it is secured by a set screw 136. Lever 134 is mounted by a bolt 138 secured to carriage 100 to secure it in the desired position to hold chain 130 taut. Chain 130 passes around an idler 144 having hemispherical portions 146 for the reception of chain 130 and also passes around drive wheel 148 which likewise has semi-hemispherical portions 150 for the reception of chain 130. Drive wheel 148 is driven by a reversible motor indicated at 152. The other end of chain 130 passes through an opening 156 in a block 158 rigidly secured to carriage 100 and is secured therein by a set screw shown at 160.

A cam 170 has a slot 172 through which passes a bolt 174 to adjustably secure the cam to carriage 100. Cam 170 is adapted to engage operating lever 176 of switch 178 and operating lever 180 of switch 182. The operation of these switches will be detailed in connection with a discussion of the wiring diagram discussed hereinafter. The operation of motor 152 is controlled by an automatically resetting timer shown at 184 having a control knob 186 for setting the desired time interval during which the motor 152 is to remain stopped. Timer 184 is a conventional zero to five hour type such as is available from the Eagle Signal Company of Moline, Illinois.

A housing 200 has a downwardly extending plate 202 which is fixedly secured to carriage 100. An inverted V guide member 204 (see FIGS. 3 and 4) has a trough 206 the lower end of which overlies the row of funnels 62 and a trough 208 the lower end of which overlies the row of funnels 54. A rigid tube 210 is mounted above guide 204 passing through a bore 212 in member 214 to which it is secured by a set screw 216. Member 214 is fixedly secured as by welding to a rod 218 (FIG. 3), for example, by welding, rod 218 being rotatably mounted in an opening 220 in housing 200 and being received in a bore 222 of a right angled lever 224 to which it is secured by a set screw 226. Lever 224 has a bifurcated end 230 which receives the operating member 232 of a solenoid 234 mounted in housing 200. Member 232 is connected to lever 224 by a pin 236 received in a slot 237 (FIG. 7) in lever 224 to permit the free pivoting of lever 224. An extension coil spring 240 is connected to housing 200 and to lever 224 to bias lever 224 in the clockwise direction as viewed in FIG. 7, i.e. to position tube 210 with its lower end over trough 208 of guide 204 when the solenoid is inactivated.

A switch 250 (FIG. 3) mounted on carriage 100 has an operating lever 252 which is spring biased upwardly and carries a cam follower roller 254 which engages the underside of rod 108 which is provided with spaced recesses 256 for the reception of roller 254. Switch 250 cooperates with timer 184 as will be detailed later.

Figure 9:
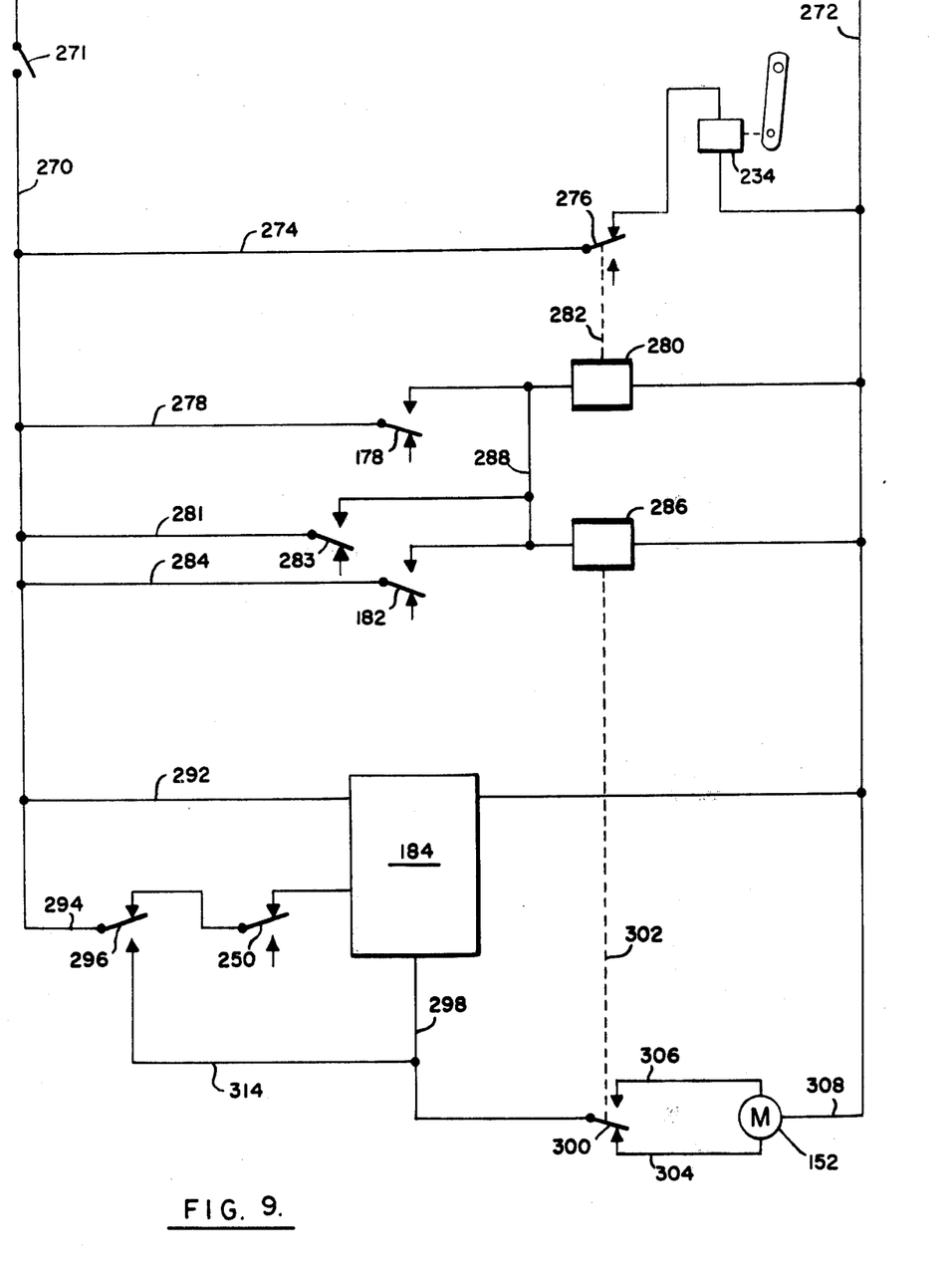
FIG. 9 is a schematic wiring diagram.

Referring now to FIG. 9, lines 270 and 272 are in a 115 volt power system, line 270 having a main power switch 271. Line 274 is connected between lines 270 and 272 and contains a switch 276 and solenoid 234. Line 278 is connected to lines 270 and 272 and contains switch 178 which is biased open and latching relay 280 which is mechanically connected to switch 276 as indicated at 282. Line 281 connects line 270 to line 288 and contains a switch 283 biased to the open position. Line 284 is connected to lines 270 and 272 and contains switch 182 which is biased open and latching relay 286.

Line 292 connects lines 270 and 272 and contains automatic resetting interval timer 184.

Line 294 contains override switch 296 and cam actuated switch 250 and is connected to interval timer 184. Timer 184 is connected by line 298 to switch 300 which is controlled by latching relay 286 as indicated by a broken line 302. Switch 300 connects line 298 to line 306 or line 304 which are connected to the split phase reversible motor 152 which is connected to line 272 by line 308. Such motors are widely available, for example, from B and B Motor Corp., New York City, N. Y. When line 304 is connected to line 298 by switch 300 motor 152 drives in a direction to advance carriage 100 away from timer 184 or to the left as viewed in FIG. 3 while when line 306 is connected to line 298 by switch 300 the motor 152 rotates in the opposite direction to move the carriage 100 in the direction towards timer 184 or to the right as viewed in FIG. 3. A line 314 connects line 298 to the other side of switch 296 to provide for energizing motor 152 through the use of override switch 296.

Timer 184 supplies power to line 298 for the running of motor 152 until switch 250 opens which causes the timer to open the circuit to line 298 and stop motor 152 for a predetermined period of time at the end of which the circuit is closed and power is resupplied to line 298 with the timer automatically resetting itself. such timers are conventional and hence timer 184 need not be described in any further detail.

OPERATION

The first step is to connect rigid tube 210 to a flexible tube 320 which provides liquid from a chromatographic column (not shown). Flexible tube 320 will be of sufficient length to provide for the travel of carriage 100. To commence operating, timer 184 is set to the desired dwell time, for example 15 minutes. Assuming by way of illustration that the tube 210 is over a funnel 62, the main power switch 271 will be closed causing the motor to drive the carriage to the left as viewed in FIG. 3. Switch 283 is momentarily closed to provide a pulse of energy to relays 280 causing the release of its latch and the opening of switch 276 to deactivate solenoid 234 and permit the shifting of lever 224 with the help of spring 240 to rotate member 214 and shift tube 210 to a position over the row of funnels 54. At the same time a pulse of energy is provided to latching relay 286 causing the shifting of switch 300 from line 304 to line 306 and the reversal of motor 152 to move the carriage 100 to the right as seen in FIG. 3. Relay 286 latches and holds switch 300 in this position. Override switch 296 is then held closed until the carriage 100 brings cam 170 into contact with operating lever 180 to close switch 182 when it is released to return to its original position. This causes a pulse of energy to relay 280 to close switch 276 and to latch to hold it closed which causes the energizing of solenoid 234 and the movement of lever 224 against the action of spring 240 to again position the tube 210 over the trough 206 of guide member 204. Simultaneously a pulse of energy is delivered to relay 286 causing it to unlatch and change switch 300 from line 306 to line 304 causing motor 152 to reverse direction. The carriage 100 moves to the left as seen in FIG. 3 until roller 254 is carried out of the first recess 256 to close switch 250 and actuate timer 184. The parts are now in the positions shown in the drawings. At this time the valve on the chromatographic column (not shown) is opened to provide a flow of liquid through tubes 320 and 210, trough 206 of guide member 204 and into the first funnel 62. The acutation of timer 184 prevents the flow of power into line 298 keeping motor 152 from operating. After a predetermined period of time of, for example, 15 minutes, timer 184 closes the circuit to line 298 and resets itself thus initiating the operation of motor 152 to advance carriage 100 through the movement of roller chain 130. Spring biased lever 122 keeps roller 120 in tight engagement with rod 108 irrespective of whether roller 120 is in or out of a recess 256. As carriage 100 advances switch 250 is opened as roller 254 moves into the next recess 256 thus again opening line 294 to timer 184. Shortly thereafter roller 254 moves out of recess 256 to again close switch 250 causing the actuation of timer 184 to shut off power from motor 152 again for the predetermined period of time. At this stage the trough 206 of guide 204 is at rest over the next funnel 62. This cycle is repeated until there has been a discharge into the last funnel 62 at which time the subsequent movement of carriage 100 causes cam 170 to engage switch arm 176 and close switch 178 providing a pulse of energy to latching relay 280 causing the release of the latch and the opening of switch 276 permitting spring 240 to shift lever 224 to cause the rotation of member 214 to shift tube 210 so as to discharge into trough 208 of guide member 204 thus causing discharge into funnels 54. At the same time the closing of switch 178 through line 278, line 288 and line 284 causes a pulse of energy to go to latching relay 286 resulting in shifting of switch 300 from line 304 to line 306 and the reversal of the direction of drive of motor 152. Relay 286 latches and holds switch 300 in this position even after the motor carries carriage 100 in the reverse direction to cause cam 170 to move away from switch arm 176 permitting switch 178 to open again. The carriage is moved stepwise incident to the function of cam switch 250 in connection with recesses 256 and the timer 184 as it did during the advance causing the discharge of liquid into one funnel 54 after another until cam 170 is carried into contact with switch arm 180 closing switch 182 causing a pulse of energy to relay 280 to close switch 276 and to latch to hold it closed which causes the energizing of solenoid 234 and the movement of lever 224 against the action of spring 240 to again position the tube 210 over the trough 206 of guide member 204. Simutaneously a pulse of energy is delivered to relay 286 causing it to unlatch and change switch 300 from line 306 to line 304 causing motor 152 to reverse direction thus initiating another cycle.

It will be understood that the above described embodiment is illustrative and that it is not intended to be limited except as set forth in the claims.

We claim:

1. A liquid fraction collector comprising:
    a first series of containers,
    a second series of containers,
    a conduit leading upwardly from each container in said first series with the upper ends of the conduits lying in a first row,
    a conduit leading upwardly from each container in said second series with the upper ends of the conduits lying in a second row parallel to the first row,
    a carriage,
    a stationary carriage support parallel to said rows and supporting the carriage above said rows for movement along a straight line at a fixed distance from each row,
    means mounted on the carriage to discharge a liquid comprising an inverted V guide member having one trough over one row and another trough over the other row and a discharge tube having a discharge end,
    means to advance the carriage along a straight line on the stationary support stepwise from one conduit to the next and return it stepwise along said straight line on the stationary support to said one end, and
    means mounted on the carriage to adjust the discharge means to discharge into the conduits of one row as the carriage advances and to change the adjustment to cause discharge into the conduits of the other row when the carriage returns,
    said last mentioned means comprising means to move the discharge end of the discharge tube relative to the carriage from a position over one trough of the guide member to a position over the other trough of the guide member when the direction of movement of the carriage is reversed.

2. A collector in accordance with claim 1 in which the means to advance the carriage stepwise comprises a reversible motor, a motor circuit to supply power to the motor, a timer in the motor circuit, a cam fixedly mounted adjacent the carriage, a switch on the carriage controlling the timer and responsive to said cam, and switch means mounted in the path of the carriage and engageable by the carriage to reverse the motor when the carriage reaches the end of a row.

3. A collector in accordance with claim 1 in which the first series of containers are arranged in a plurality of groups with means to support each group at a different elevation.

4. A collector in accordance with claim 1 in which the means to move the discharge end of the discharge tube comprises rotatably mounted support means to support said tube on the carriage, motor means to rotate the support means through a predetermined angle, switch means to activate the motor means when the carriage reaches one end of the rows and switch means to cause the motor means to return to its original position when the carriage reaches the other end of the rows.

5. A liquid fraction collector comprising:
    a frame,
    a first series of containers,
    a second series of containers,
    each of the first and second series of containers being arranged in a plurality of groups with means to support each group on the frame at a different elevation,
    a conduit leading upwardly from each container in said first series with the upper ends of the conduits lying in a first row,
    a conduit leading upwardly from each container in said second series with the upper ends of the conduits lying in a second row parallel to the first row,
    a carriage mounted on the frame above said conduits,
    means mounted on the carriage to discharge a liquid comprising an inverted V guide member having one trough over one row and another trough over the other row, a discharge tube having a discharge end movable from a first position over one trough of the guide member to a second position over the other trough of the guide member,
    means to advance the carriage along a straight line stepwise from one conduit to the next above the said rows from one end of the rows to the other end and return it along said straight line stepwise to said one end comprising a reversible motor, a motor circuit to supply power to the motor, a timer in the motor circuit, a cam mounted on the frame adjacent the carriage, a switch on the carriage controlling the timer and responsive to said cam and switch means on the frame and engageable by the carriage to reverse the motor when the carriage reaches the end of a row, means to hold the discharge end of the tube in the first position as the carriage advances and in the second position as the carriage returns comprising rotatably mounted support means to support said tube on the carriage with the discharge end in the first position, motor means to rotate the support means through a predetermined angle to position the discharge end of the tube in the second position, switch means to activate the motor means when the carriage reaches one end of the rows and switch means to cause the motor means to return to its original position when the carriage reaches the other end of the rows.

* * * * *